United States Patent [19]

Loiacono

[11] Patent Number: 4,782,182

[45] Date of Patent: Nov. 1, 1988

[54] METHOD OF PRODUCING CRYSTALS OF L-ARGININE PHOSPHATE MONOHYDRATE

[75] Inventor: Gabriel M. Loiacono, Franklin Lakes, N.J.

[73] Assignee: North American Philips Corp., New York, N.Y.

[21] Appl. No.: 98,435

[22] Filed: Sep. 16, 1987

Related U.S. Application Data

[63] Continuation-in-part of Ser. No. 841,129, Mar. 18, 1986, abandoned.

[51] Int. Cl.$^4$ ............................................. C07C 129/08
[52] U.S. Cl. .................................................... 562/560
[58] Field of Search ......................................... 562/560

[56] References Cited

PUBLICATIONS

Aoki, Acta Cryst., Sect. B, 27(1) pp. 11–23 (1971).
Min–hua, VII International Conference on Crystal Growth, Stuttgart, Germany, pp. 12–16 (1983).
Kirk-Othmer, "Encyclopedia of Chemical Technology," vol. 6, pp. 482–498 +513–515 (1965).
Loiacono, J. Crystal Growth, 46 pp. 105–111 (1979).
Delfino, J. Solid State Chem., 20 pp. 391–395 (1977).
Finar, "Organic Chemistry," vol. 1, pp. 61–62 (1973).

*Primary Examiner*—Michael L. Shippen
*Attorney, Agent, or Firm*—Norman N. Spain

[57] ABSTRACT

Large flaw-free crystals of L-arginine phosphate monohydrate (LAP) are produced from a saturated aqueous solution of LAP by rotating seed crystals of LAP in the solution while maintaining the pH of the solution at 2–8, preferably at 2–3 while lowering the temperature of the solution at a rate of 0.01° C.–1° C. until crystallization is completed.

5 Claims, No Drawings

METHOD OF PRODUCING CRYSTALS OF L-ARGININE PHOSPHATE MONOHYDRATE

RELATED APPLICATIONS

This application is a continuation-in-part of application Ser. No. 841,129, filed Mar. 18, 1986, now abandoned.

BACKGROUND OF THE INVENTION

This invention relates to a method of producing crystals of L-arginine phosphate monohydrate (hereinafter termed LAP).

LAP is a known material which has been shown by Jiang Min-hua et al VII International Conference on Crystal Growth Stuttgart, Germany 12-16 1983 Program and Abstracts to crystallize in the monoclinic system. Further, this Jiang Min-hua et al article states that these LAP crystals are phase-matchable non-linear optical crystals having excellent stability towards moisture as well as having a high optical damage threshold. As a result, these materials are considered to be useful as optical frequency doublers and frequency modulators.

The Jiang Min-hua et al article also shows further, that by cooling and evaporating methods, LAP single crystals of the size of $13 \times 35 \times 35$ mm have been prepared. However, it is desirable for many applications to have as flaw-free of LAP crystals of even larger size as possible.

SUMMARY OF THE INVENTION

A principal object of this invention is to provide a method for the production of large flaw-free LAP crystals. These and other objects of this invention will be apparent from the description that follows.

According to this invention there is provided a novel method of growing LAP crystals from a solution. Briefly, according to the method of this invention, a saturated aqueous solution of LAP is prepared at a temperature of from 20° C. to 80° C. The pH of the solution is adjusted to 2-8. Seed crystals of LAP are then suspended in the saturated solution and rotated at a rate of from 5 rpm to 50 rpm. The temperature of the solution is then lowered at a rate of from 0.01° C. to 1° C. per day until crystal growth is completed.

By use of this method, flaw-free LAP crystals of excellent optical quality and as large as $40 \times 60 \times 20$ mm or more may be obtained.

DETAILED DESCRIPTION OF THE INVENTION

While good results are obtained at a pH of the solution of from 2 to 8, it has been found that best results are obtained at a pH range of from 2 to 3. Preferably, the pH is adjusted by the addition to the solution of phosphoric acid.

Additionally, it has been found that best results are obtained when the temperature of the solution is lowered at a rate of from 0.050° C. per day to 0.5° C. per day the actual rate of decrease depending among other things on the starting temperature of the solution, the rate of rotation of the seed crystals and the desired size of the crystals to be produced. The rate of temperature lowering may remain constant or may be increased, generally in a step-wise manner, during the crystallization process.

Both oriented and non-oriented seed crystals may be employed.

Preferably, to produce crystals of optimum purity the LAP material used to form the saturated solution is recrystallized at least once.

If it is desired to shift the frequency resonance of the crystals, or for other purposes, deuterium may be substituted for ionizable hydrogen, at least in part, by employing heavy water to form the saturated solution in which a desired concentration of deuterium is present.

For better understanding of the invention, the novel method of the invention will now be described in greater detail in the following example:

EXAMPLE

L-arginine phosphate monohydrate (LAP) of the formula: $C_6H_{14}N_4O_2.H_3PO_4.H_2O$ was synthesized by reacting 2.87 mols of L-arginine (Sigma Chemical No. A-5006) with 2.87 mols of phosphoric acid, ($H_3PO_4$ 85%) in aqueous solution at 50° C. The mixture was stirred at 200 rpm for four hours. The resultant compound was allowed to precipitate out, filtered and recovered. The compound was then recrystallized in water.

A crystal growth solution was then prepared by producing a saturated aqueous solution of the recrystallized compound at 46% and adjusting the pH of the saturated solution with $H_3PO_4$ to a value of 2.3. The saturated solution was then heated to 58° C., filtered and held at least 24 hours at that temperature.

A Holden type crystallizer (or other suitable apparatus) was then loaded with random oriented seed crystals of LAP monohydrate and heated to 48° C. The saturated solution was then cooled to 48° C. and transferred to the growth chamber of the crystallizer. After the system reached equilibrium, the seed crystals were lowered into the solution, rotation of the seeds was initiated at 15 RPM and a temperature lowering program for the solution was initiated, starting at 0.050°/day over a period of 30 days, the temperature lowering rate was increased stepwise to a maximum of 0.5° C./day.

After the crystal growth was completed, the solution was removed from the growth chamber, the grown crystals were cooled to room temperature at 10° C./day and were removed from the growth chamber. It was found that flaw-free LAP crystals as large as $38 \times 56 \times 16$ mm were produced.

It will be apparent that various modifications may be made to the present invention without departing from its scope as defined in the following claims.

What is claimed:

1. A method of producing large, optical quality crystals of L-arginine phosphate monohydrate, said method comprising:
   (a) dissolving a sufficient quantity of L-arginine phosphate monohydrate in water to form a saturated aqueous solution of said L-arginine phosphate monohydrate at a temperature of 20° C.–80° C.;
   (b) adjusting the pH of said solution to 2–3;
   (c) suspending seed crystals of said L-arginine phosphate monohydrate in said solution and rotating said seed crystals at a rate of from 5 RPM to 50 RPM, and
   (d) lowering the temperature of said solution at a rate of 0.01° C.–1° C. per day until crystallization is completed.

2. The method of claim 1 wherein the L-arginine phosphate monohydrate used in forming the saturated solution is recrystallized at least once prior to its use in the formation of said saturated solution.

3. The method of claim 1 wherein the pH of the saturated solution is adjusted to about 2.3.

4. The method of claim 1 wherein the temperature of the solution is lowered at a rate of from 0.05° C.–0.5° C. per day.

5. The method of claim 1 wherein the deuterium normally present in L-arginine phosphate monohydrate is increased by replacing the water employed in forming the saturated solution with heavy water in which the ratio of deuterium to hydrogen corresponds to the ratio of deuterium to ionizable hydrogen to be provided in the resultant crystallized L-arginine phosphate monohydrate.

* * * * *